(12) United States Patent
Brown et al.

(10) Patent No.: US 12,731,678 B2
(45) Date of Patent: Sep. 8, 2026

(54) SYSTEMS AND METHODS FOR LOCALIZING RETAINED SURGICAL ITEMS COMBINING RFID TAGS AND COMPUTER VISION

(71) Applicant: Covidien LP, Mansfield, MA (US)

(72) Inventors: Christopher T. Brown, Boulder, CO (US); Jason M. Mucilli, Lakewood, CO (US)

(73) Assignee: Covidien LP, Mansfield, MA (US)

( * ) Notice: Subject to any disclaimer, the term of this patent is extended or adjusted under 35 U.S.C. 154(b) by 140 days.

(21) Appl. No.: 17/873,202

(22) Filed: Jul. 26, 2022

(65) Prior Publication Data

US 2023/0084032 A1 Mar. 16, 2023

Related U.S. Application Data

(60) Provisional application No. 63/243,812, filed on Sep. 14, 2021.

(51) Int. Cl.
*G16H 40/20* (2018.01)
*G06K 7/10* (2006.01)

(52) U.S. Cl.
CPC ......... *G16H 40/20* (2018.01); *G06K 7/10366* (2013.01)

(58) Field of Classification Search
None
See application file for complete search history.

(56) References Cited

U.S. PATENT DOCUMENTS

| | | | |
|---|---|---|---|
| 9,827,048 B2 | 11/2017 | Sweeney | |
| 2004/0250819 A1 | 12/2004 | Blair et al. | |
| 2006/0017545 A1* | 1/2006 | Volpi | G06K 19/0739 340/10.4 |
| 2007/0268133 A1* | 11/2007 | Sanchez | G08B 13/2462 340/568.1 |
| 2017/0337792 A1 | 11/2017 | Bermudez Rodriguez et al. | |

(Continued)

FOREIGN PATENT DOCUMENTS

| | | |
|---|---|---|
| CA | 3093300 A1 | 9/2019 |
| WO | 2018013411 A1 | 1/2018 |

OTHER PUBLICATIONS

Extended European Search Report dated Feb. 8, 2023 corresponding to counterpart Patent Application EP 22195345.8.

*Primary Examiner* — Stella Higgs
(74) *Attorney, Agent, or Firm* — Carter, DeLuca & Farrell, LLP

(57) ABSTRACT

An inventory system configured for detecting and counting potentially retained surgical items within a body of a patient includes an RFID tag configured to transmit a return signal at a frequency when energized, a signal generator configured to generate an energizing signal for the RFID tag, an antenna operably coupled to the signal generator, the antenna configured to receive a return signal transmitted by the RFID tag, an imaging device configured to capture an image, a processor, and a memory. The memory includes instructions stored thereon, which when executed by the processor cause the system to energize the RFID tag, receive the return signal from the antenna, receive the image of the area including the portion of the body of the patient from the imaging device, and determine a spatial location of the RFID tag.

19 Claims, 8 Drawing Sheets

(56) References Cited

U.S. PATENT DOCUMENTS

| | | | | |
|---|---|---|---|---|
| 2019/0021677 | A1* | 1/2019 | Grbic | G06T 7/11 |
| 2020/0302576 | A1* | 9/2020 | Xu | G06N 3/084 |
| 2020/0364660 | A1 | 11/2020 | Hines et al. | |
| 2021/0004744 | A1* | 1/2021 | Petrany | G07C 5/008 |
| 2021/0312621 | A1* | 10/2021 | Chou | G01N 15/1433 |
| 2021/0392608 | A1* | 12/2021 | Swope | G01S 5/0252 |
| 2023/0161981 | A1* | 5/2023 | Son | G06K 7/10316<br>235/451 |

* cited by examiner

SYSTEMS AND METHODS FOR LOCALIZING RETAINED SURGICAL ITEMS COMBINING RFID TAGS AND COMPUTER VISION

FIELD

The present disclosure relates generally to interrogation and detection systems for radio-frequency (RF) tags, and more particularly, detection and inventory systems for potentially retained surgical items within surgical sites.

BACKGROUND

It is often useful to determine whether objects associated with a surgery are present in a patient's body before completion of the surgery. Such objects may take a variety of forms. For example, the objects may take the form of instruments, for instance, scalpels, scissors, forceps, hemostats, and/or clamps. Also, for example, the objects may take the form of related accessories and/or disposable objects, for instance, surgical sponges, gauzes, and/or pads. Failure to locate an object before closing the patient may require additional surgery, and in some instances, may have unintended medical consequences.

Accordingly, there is a need for a technology that is capable of providing both presence detection and tagged surgical item/implement identification functionality in the medical setting, as well as inventory controls of the tagged items/implements. Specifically, detecting the presence of, identifying, and maintaining inventory of tagged surgical items and materials that are used during the execution of a medical procedure. Technologies exist that enable these functions both individually as well as in conjunction with each other, but the methods and packaging of the discrete solutions used are not ideal for the application. More specifically, the components attached or affixed to the items being tracked are either too large physically and present nuisances or obstacles in the execution of the procedure, or the detection and identification performance of the solution may degrade rapidly in the presence of variable and uncontrolled dielectric or conductive materials.

Accordingly, there are needs for improvements in presence detection, tagged item identification, and inventory functionality in the medical setting.

SUMMARY

This disclosure relates to systems for detection of surgical items and/or devices used in body cavities during surgery, specifically systems that include an antenna to be inserted directly into a surgical site to detect such surgical items and/or devices.

In accordance with aspects of the disclosure, an inventory system configured for detecting and counting potentially retained surgical items includes an RFID tag configured to transmit a return signal when energized, a signal generator configured to generate an energizing signal for the RFID tag, an antenna operably coupled to the signal generator, the antenna configured to receive at least one return signal transmitted by the RFID tag, an imaging device configured to capture an image of an area, a processor, and a memory. The memory includes instructions stored thereon, which when executed by the processor cause the system to energize the RFID tag, receive the return signal from the antenna, capture the image of the area including at least the portion of the body of the patient from the imaging device, and determine a spatial location of the RFID tag based on the image and the received signal.

In an aspect of the present disclosure, the system may further include a display. The instructions, when executed by the processor, may further cause the system to display the determined spatial location of the RFID tag on the display.

In another aspect of the present disclosure, the RFID tag may include a unique identifier.

In yet another aspect of the present disclosure, the instructions, when executed by the processor, may further cause the system to determine a characteristic of the RFID tag based on the unique identifier.

In a further aspect of the present disclosure, the instructions, when executed by the processor, may further cause the system to determine a quantity of unique RFID tags based on the unique identifier of each unique RFID tag of the quantity of RFID tags.

In yet a further aspect of the present disclosure, the RFID tag may include a visual marker.

In an aspect of the present disclosure, the captured image may include the visual marker. The instructions, when executed by the processor, may further cause the system to determine a unique characteristic of the RFID tag based on the visual marker.

In yet another aspect of the present disclosure, the instructions, when executed by the processor, may further cause the system to predict an identity of an object based on the image using a machine learning network and/or a computer vision model.

In a further aspect of the present disclosure, when determining the spatial location of the RFID tag the instructions, when executed by the processor, may further cause the system to predict the spatial location of the RFID tag based on the predicted identity of the object and the received signal using the machine learning network and/or a computer vision model.

In yet a further aspect of the present disclosure, the instructions, when executed by the processor, may further cause the system to predict a body region of the patient based on the image using a machine learning network.

In accordance with aspects of the disclosure, a computer-implemented method for detecting and counting potentially retained surgical items within a body of a patient, includes energizing an RFID tag, the RFID tag configured to transmit a return signal when energized, receiving the return signal from an antenna, the antenna operably coupled to a signal generator, the antenna configured to receive at least one return signal transmitted by the RFID tag, capturing an image of an area including at least a portion of the body of the patient from an imaging device, the imaging device configured to capture an image of an area including at least a portion of a body of the patient, and determining a spatial location of the RFID tag based on the image and the received signal.

In another aspect of the present disclosure, the method may further include displaying the determined spatial location of the RFID tag on the display.

In yet another aspect of the present disclosure, the RFID tag includes a unique identifier.

In a further aspect of the present disclosure, the method may further include determining at least one characteristic of the RFID tag based on the unique identifier.

In yet a further aspect of the present disclosure, the method may further include determining a quantity of unique RFID tags based on the unique identifier of each unique RFID tag of the quantity of RFID tags.

In an aspect of the present disclosure, the RFID tag may include a visual marker.

In an aspect of the present disclosure, the captured image may include the visual marker. The method may further include determining a unique characteristic of the RFID tag based on the visual marker.

In an aspect of the present disclosure, the method may further include predicting an identity of an object based on the image using a machine learning network.

In accordance with aspects of the disclosure, when determining the spatial location of the RFID tag, the method may further include predicting the spatial location of the RFID tag based on the predicted identity of the object and the received signal using the machine learning network.

In accordance with aspects of the disclosure, a non-transitory computer-readable medium storing instructions which, when executed by a processor, cause the processor to perform a method for detecting and counting potentially retained surgical items within a body of a patient includes energizing an RFID tag, the RFID tag configured to transmit a return signal when energized, receiving the return signal from an antenna, the antenna operably coupled to a signal generator, the antenna configured to receive at least one return signal transmitted by the RFID tag, receiving an image of an area including at least a portion of the body of the patient from an imaging device, the imaging device configured to capture an image of an area including at least a portion of a body of the patient, and determining a spatial location of the RFID tag based on the image and the received signal.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements and have been solely selected for ease of recognition in the drawings.

Various aspects of the presently disclosed antennae, RFID tags, and articles containing them are described hereinbelow with reference to the drawings.

DETAILED DESCRIPTION

In the following description, certain specific details are set forth in order to provide a thorough understanding of disclosed aspects. However, one skilled in the relevant art will recognize that aspects may be practiced without one or more of these specific details or with other methods, components, materials, etc. In other instances, well-known structures associated with transmitters, receivers, or transceivers have not been shown or described in detail to avoid unnecessarily obscuring descriptions of the aspects.

Reference throughout this specification to "one aspect" or "an aspect" means that a particular feature, structure, or characteristic described in connection with the aspect is included in at least one aspect. Thus, the appearances of the phrases "in one aspect" or "in an aspect" in various places throughout this specification are not necessarily all referring to the same aspect. Furthermore, the particular features, structures, or characteristics may be combined in any suitable manner in one or more aspects.

Figure 1:
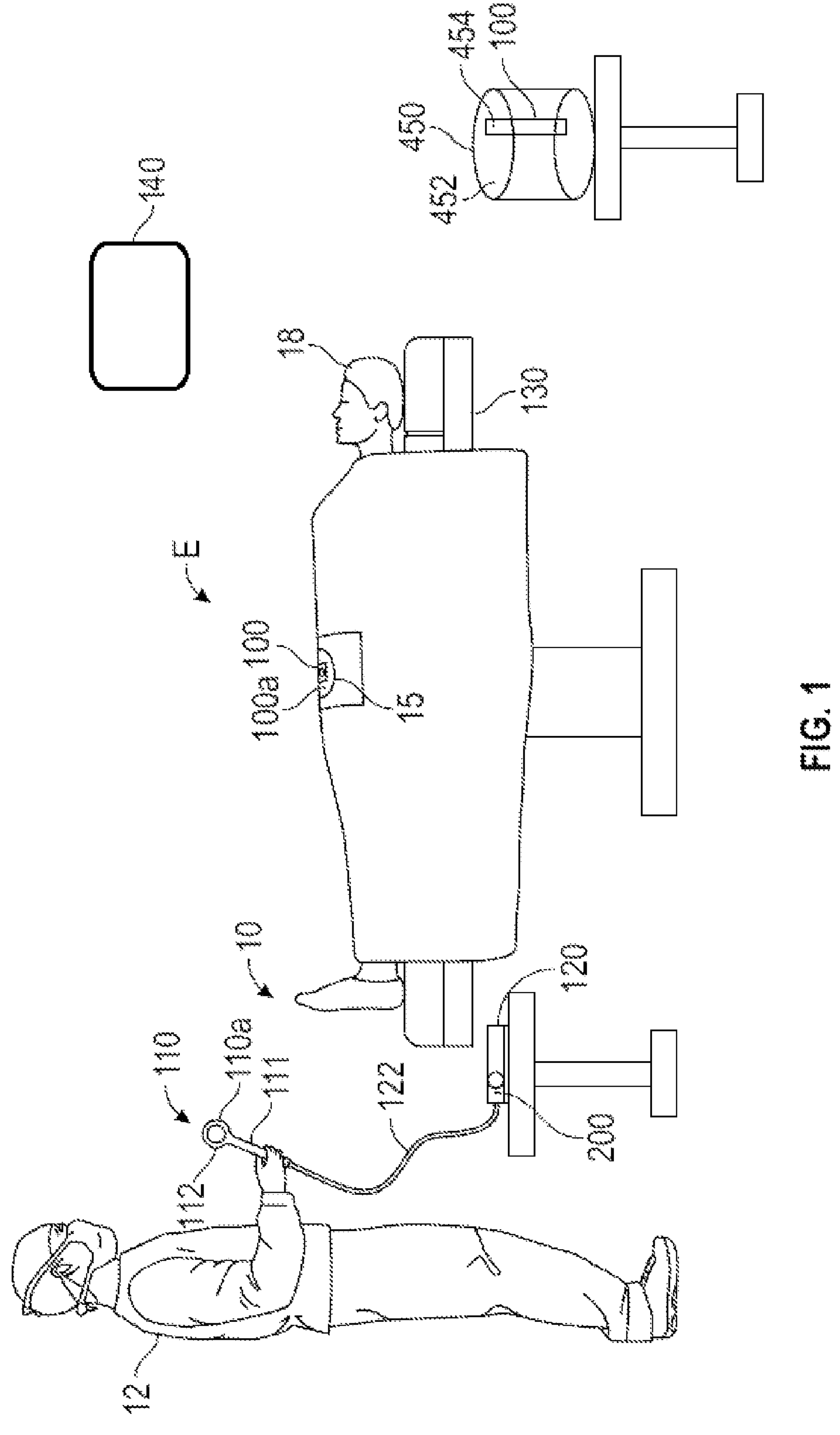
FIG. 1 is a schematic diagram showing a surgical environment illustrating a medical provider using an inventory system for detecting and counting an object within a patient that is tagged with an RFID tag according to one illustrated aspect.

FIG. 1 depicts a surgical environment "E" in which a medical provider 12 operates an inventory system 10 for detection and counting of radio-frequency identification (RFID) tags 100 to ascertain the presence or absence of items, implements, or objects 100*a* in a patient 18. The inventory system 10 may include a signal generator 120 and an antenna 110 coupled to the signal generator 120 by one or more communication paths, for example, coaxial cable 122. In one aspect of the inventory system 10, the antenna 110 may take the form of a hand-held wand 110*a*.

The object 100*a* may take a variety of forms, for example, instruments, accessories, and/or disposable objects useful in performing surgical procedures. For instance, the object 100*a* may take the form of scalpels, scissors, forceps, hemostats, and/or clamps. Also, for example, the objects 100*a* may take the form of surgical sponges, gauze, and/or padding. The object 100*a* is tagged, carrying, attached, or otherwise coupled to an RFID tag 100. Aspects of the inventory system 10 disclosed herein are particularly suited to operate with one or more RFID tags 100, which are not accurately tuned to a chosen or selected resonant frequency.

In use, the medical provider 12 may position the wand 110*a* approximate the patient 18 in order to detect the presence or absence of the one or more RFID tags 100 and hence an object 100*a*. The medical provider 12 may, in some aspects, move the wand 110*a* along and/or across the body of the patient 18. For a detailed description of an exemplary inventory system, reference may be made to commonly owned U.S. Patent Application Publication No. 2004/0250819 to Blair et al., entitled "Apparatus and Method for Detecting Objects Using Tags and Wideband Detection Device," filed Mar. 29, 2004, the entire contents of which is hereby incorporated by reference herein.

The system 10 may include a display 140 configured to display images and/or other data. The system 10 may include an imaging device 111 configured to capture an image of an area, the area including at least a portion of a body of the patient 18.

Figure 2:
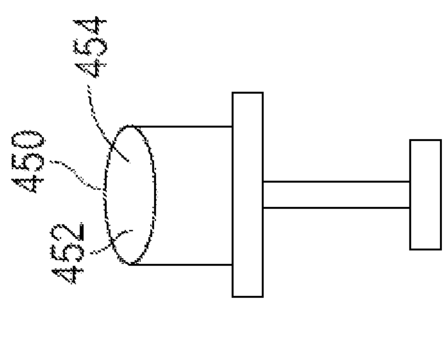
FIG. 2 is a schematic illustration of an antenna for detection of surgical implements within a patient's body in active use within a surgical site.
Figure 2:
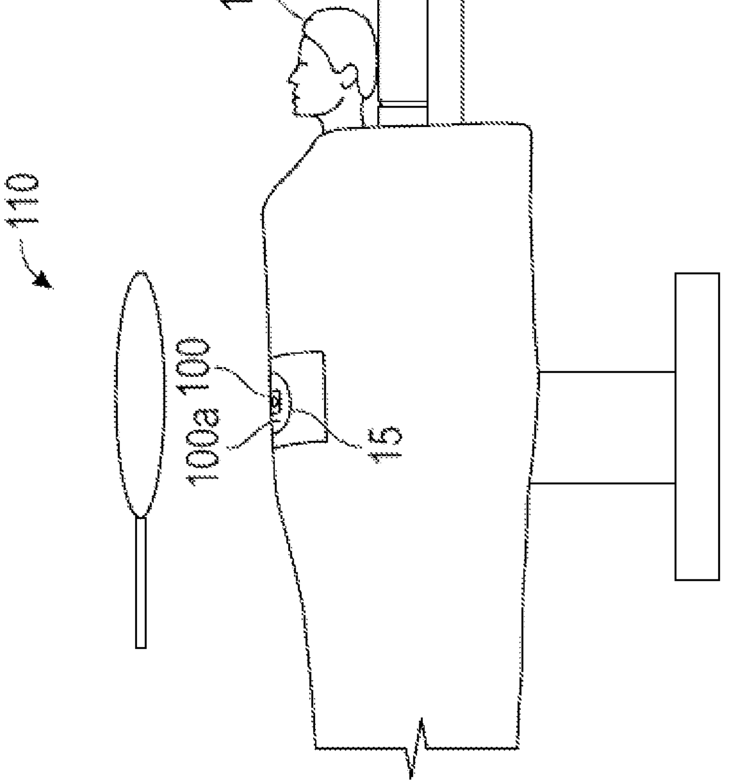

Referring now to FIG. 2, inventory system 10, for detection and counting of surgical implements (e.g., object 100*a*) within a patient's body 18, includes a signal generator 120 to provide an energizing signal for one or more dual RFID tags 100 (FIG. 1) affixed to an object 100*a* (FIG. 1). Each RFID tag 100 is configured to transmit a return signal when energized, such that an antenna 110 can detect the return signal and confirm the presence of objects 100*a* within the body of patient 18. The antenna 110 is operably coupled to the signal generator 120 via a communication cable 122, which may be of variable length to provide greater range of motion to the clinician handling the antenna 110. The signal generator 120 may include a controller 200.

In one aspect of inventory system 10, the antenna 110 is an antenna 110 configured to be waved over the surgical site 15, e.g., over the body of patient 18. For example, the antenna 110 may be held over the body of the patient 18 at the height of about four or about five inches while attempting to detect dual RFID tags 100, so that the user may detect and/or confirm the presence of objects 100*a* within the body of patient 18.

The system 10 may further include an RFID-enabled secure package 450 (e.g., RFID-enabled smart packaging and/or RFID enabled secure mutual authentication packaging), which includes an RFID tag affixed thereto. For example, an RFID tag may be secured to a lid or a body of the RFID-enabled secure package 450. The RFID tag 100 is configured to transmit a return signal when energized. Generally, the RFID-enabled secure package 450 will include a surgical object 454 (e.g., cotton swabs) configured to be removed from the RFID-enabled secure package 450. The surgical object 454 includes a retained surgical item RFID tag, e.g., the dual RFID tag 100, affixed to the surgical object 454. The surgical object 454 may include, for example, any surgical sponge, cotton swab, instrument, tool, and/or device that is unintentionally left in the patient at the completion of a surgery or other procedure.

The RFID-enabled secure package 450 includes, but is not limited to, for example, caps and closures and are generally configured to verify the contents of sealed containers to ensure the product is genuine, not part of a recall, within the expiration date, and/or has not been tampered with or diverted. RFID-enabled secure package 450 generally includes a secure package RFID tag 452.

In aspects, the retained surgical item dual RFID tag 100 may be linked to the secure package RFID tag 452 by embedding an encrypted block of data that contains the unique identifier of the RFID tag 100. For example, to enable the use of the retained surgical object 454, the RFID tag 100 may be scanned by the antenna 110 in the inventory system 10.

Figure 3:
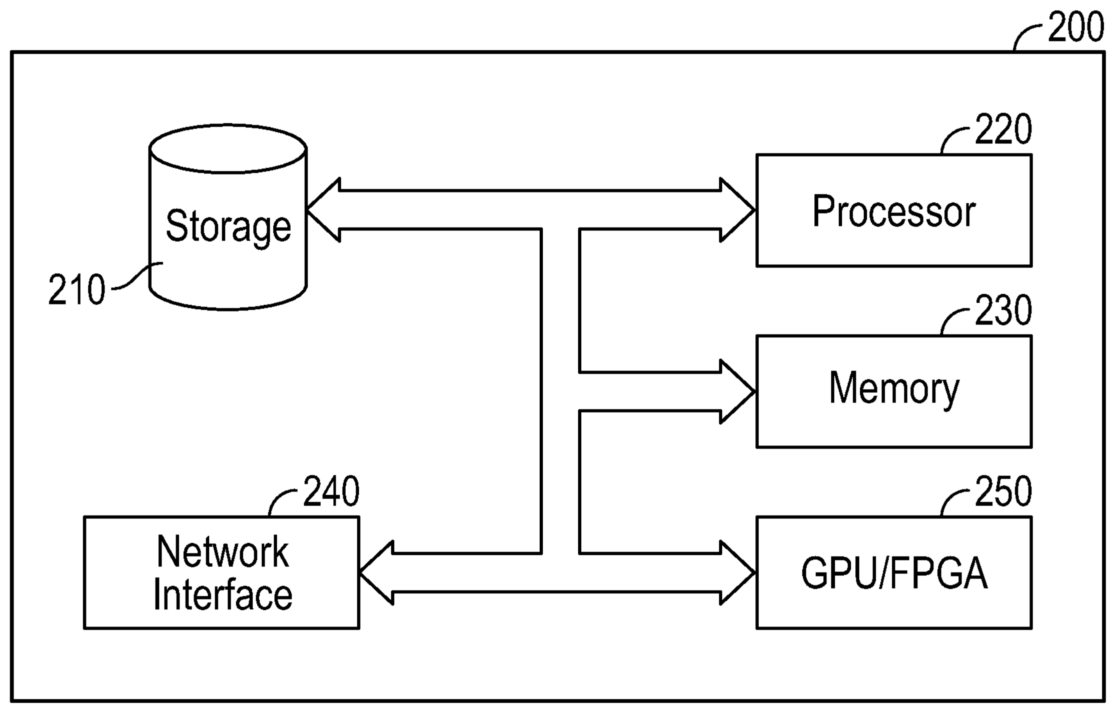
FIG. 3 is a block diagram of a controller of the system of FIG. 1.

FIG. 3 illustrates that controller 200 includes a processor 220 connected to a computer-readable storage medium or a memory 230. The computer-readable storage medium or memory 230 may be a volatile type of memory, e.g., RAM, or a non-volatile type of memory, e.g., flash media, disk media, etc. In various aspects of the disclosure, the processor 220 may be another type of processor such as, without limitation, a digital signal processor, a microprocessor, an ASIC, a graphics processing unit (GPU), a field-programmable gate array (FPGA), or a central processing unit (CPU). In certain aspects of the disclosure, network inference may also be accomplished in systems that have weights implemented as memristors, chemically, or other inference calculations, as opposed to processors.

In aspects of the disclosure, the memory 230 can be random access memory, read-only memory, magnetic disk memory, solid-state memory, optical disc memory, and/or another type of memory. In some aspects of the disclosure, the memory 230 can be separate from the controller 200 and can communicate with the processor 220 through communication buses of a circuit board and/or through communication cables such as serial ATA cables or other types of cables. The memory 230 includes computer-readable instructions that are executable by the processor 220 to operate the controller 200. In other aspects of the disclosure, the controller 200 may include a network interface 240 to communicate with other computers or to a server. A storage device 210 may be used for storing data.

Figure 4:
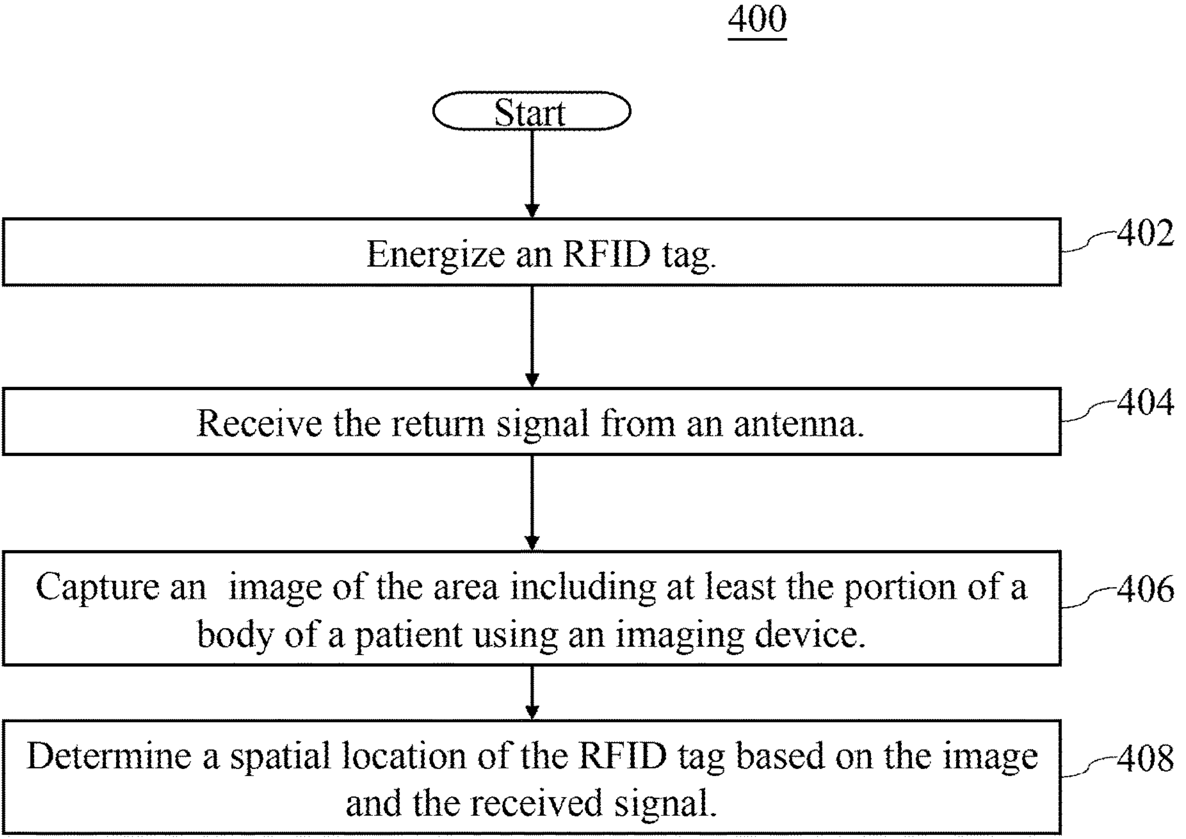
FIG. 4 is a flow chart of a computer-controlled method for detecting and counting potentially retained surgical items using the system of FIG. 1.

Referring to FIG. 4, there is shown a flow chart of an exemplary computer-implemented method 400 for detecting and counting potentially retained surgical items within a body of a patient in accordance with aspects of the present disclosure. Although the steps of FIG. 4 are shown in a particular order, the steps need not all be performed in the specified order, and certain steps can be performed in another order. For simplicity, FIG. 4 will be described below, with the controller 200 performing the operations. However, in various aspects, the operations of FIG. 4 may be performed in part by the controller 200 of FIG. 3 and in part by another device, such as a remote server. These variations are contemplated to be within the scope of the present disclosure.

The two main functions of an inventory system (such as an operating room safety system) are to detect and count potentially retained surgical items (RSIs). The term retained surgical item, as used herein, includes any surgical sponge, instrument, tool, and/or device that is unintentionally left in the patient at the completion of a surgery or other procedure. The disclosed technology detects and counts potential RSIs, each of which includes an RFID tag 100, in a secure fashion and in a way that provides individual identification to each RFID tag 100 based potential retained surgical item.

Initially, at step 402, the signal generator 120 energizes an RFID tag 100, using an antenna 110. The antenna is configured to receive a return signal transmitted by the RFID tag 100. The RFID tag 100 may include a high-frequency RFID tag, a low-frequency RFID tag, and/or an ultra-high frequency RFID tag.

In an aspect, the RFID tag 100 may be attached to a surgical object 454 (e.g., surgical gauze and/or a surgical sponge). In aspects, the system may include an RFID-enabled secure package 450 (e.g., smart packaging), which includes a set of manufactured potential RSIs 454 (such as cotton sponges). The RFID-enabled secure package 450 includes an RFID tag 452 (e.g., an RFID chip), which is capable of mutual authentication with a host (e.g., controller 200). The RFID tag 100 may include a unique identifier stored in its memory. In aspects, the RFID tag may include a visual marker. For example, the visual marker may include a symbol or a shape such as an "X," color tagging, florescence IR/UV tagging and barcoding, and/or QR coding of instruments and/or cotton may by incorporated. For example, a surgical pouch may have a coating applied to it that enables identification by the antenna 110.

Next, at step 404, the controller 200 receives the return signal from the antenna 110, which is configured to receive at least one return signal transmitted by the RFID tag 100.

In aspects, the antenna 110 may include a sensor 112 (e.g., a gyro and/or a GPS), which is configured to provide localization-based data of the antenna 110 when scanning for the RFID tag 100. The spatial parameter may further include a proximity of the antenna 110 to a patient 18.

Figure 8:
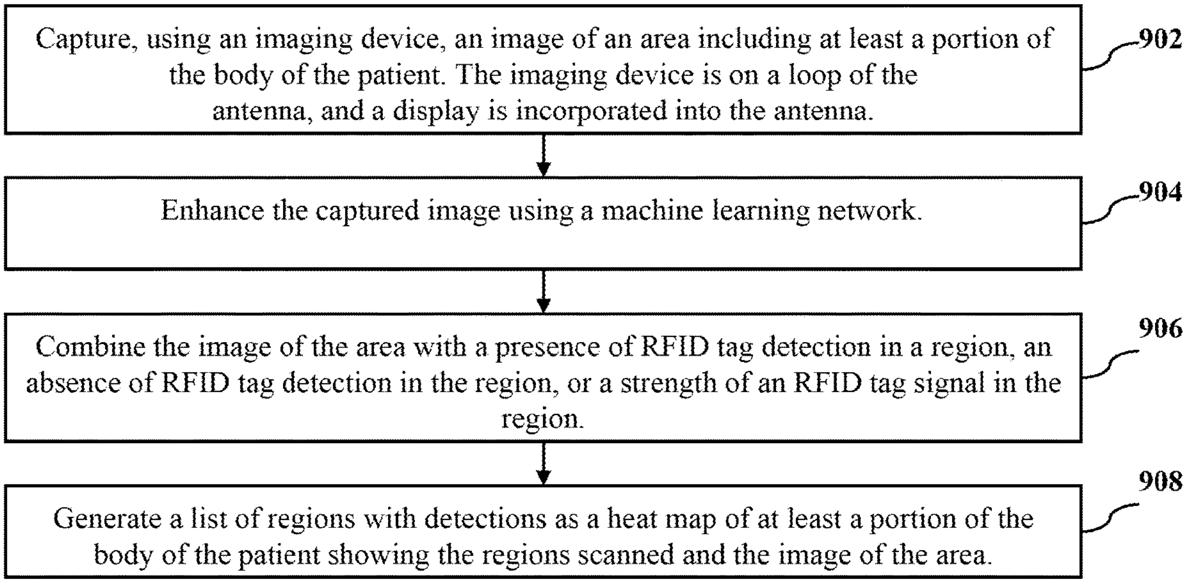
FIG. 8 is a flow chart of a computer-controlled method for generating a heat map using the system of FIG. 1.

Next, at step 902 (FIG. 8), the imaging device 111 captures an image of an area including at least a portion of the body of the patient 18. The imaging device 111 is configured to capture an image of an area including at least a portion of a body of the patient 18. Images may include a still image, a stereographic image, and/or video. The controller 200 receives, at operation 406, the image of the area from the imaging device.

The imaging device 111 may be located, for example, on the patient-facing side of a handset of the antenna 110 and/or on the loop of the antenna 110. It is contemplated that the imaging device 111 may be located on any suitable portion of the antenna 110. As the handset is moved over the patient 18, the imaging device 111 captures a series of images of the region the antenna 110 was passing over. These images may be used to construct a mosaic image of the regions observed by the antenna 110 and the path of travel of the antenna 110. In another aspect, the images may be used to detect the region of the body of the patient 18 the antenna 110 is currently over.

In aspects, the controller may determine at least one characteristic of the RFID tag 100 based on the unique identifier. The characteristic may include a signal strength, a unique surgical object type, and/or a serial number. In aspects, the controller 200 may determine a quantity of unique RFID tags based on the unique identifier of each unique RFID tag 100 of the quantity of RFID tags. In aspects, the controller 200 may determine a unique characteristic of the RFID tag 100 based on the visual marker of the RFID tag.

Next, at step 408, the controller 200 determines a spatial location of the RFID tag 100 based on the image and the received signal.

Figure 5:
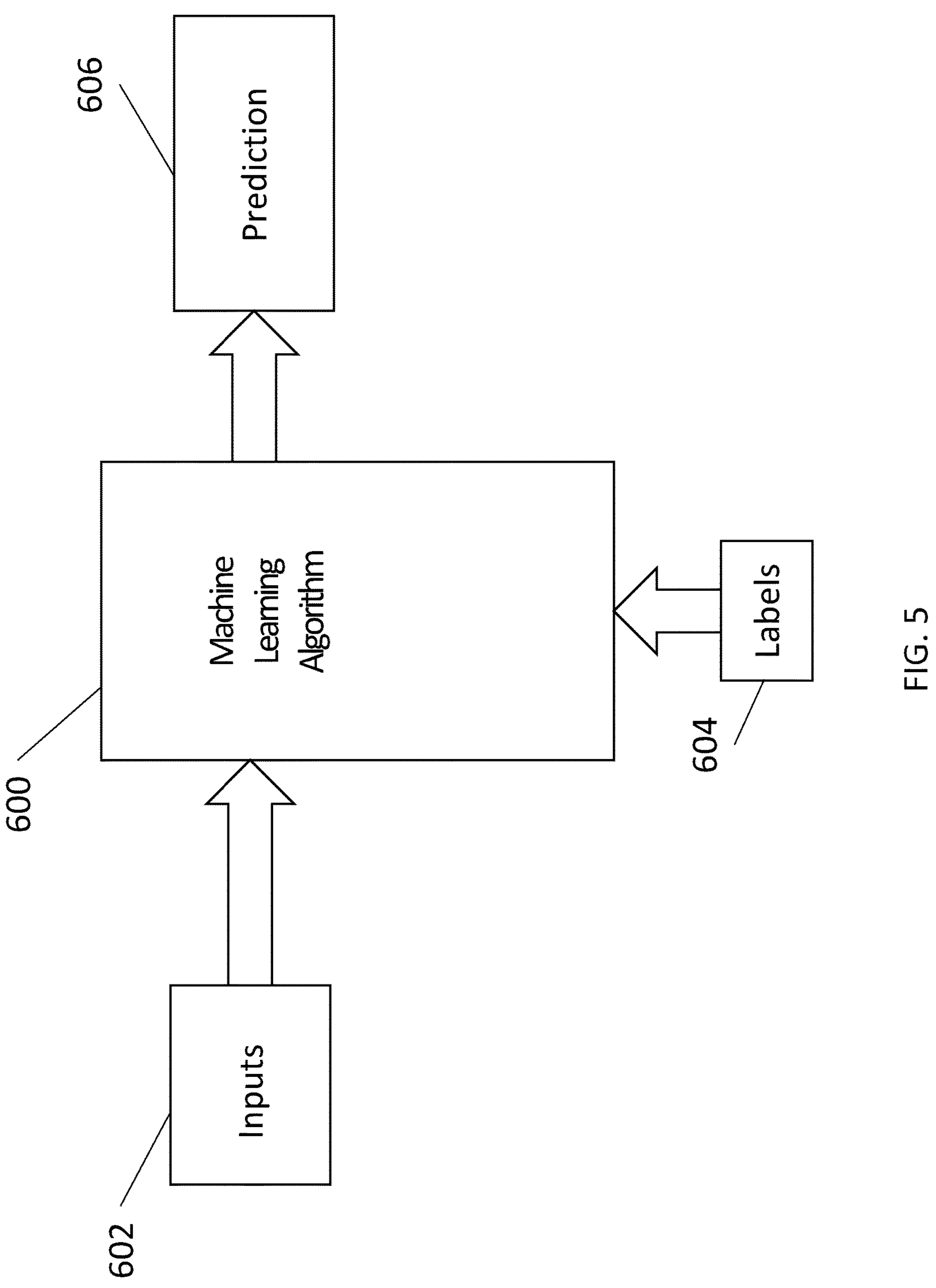
FIG. 5 is a flow diagram of a machine learning network of the computer-controlled method for detecting and counting potentially retained surgical items using the system of FIG. 1.
Figure 7:
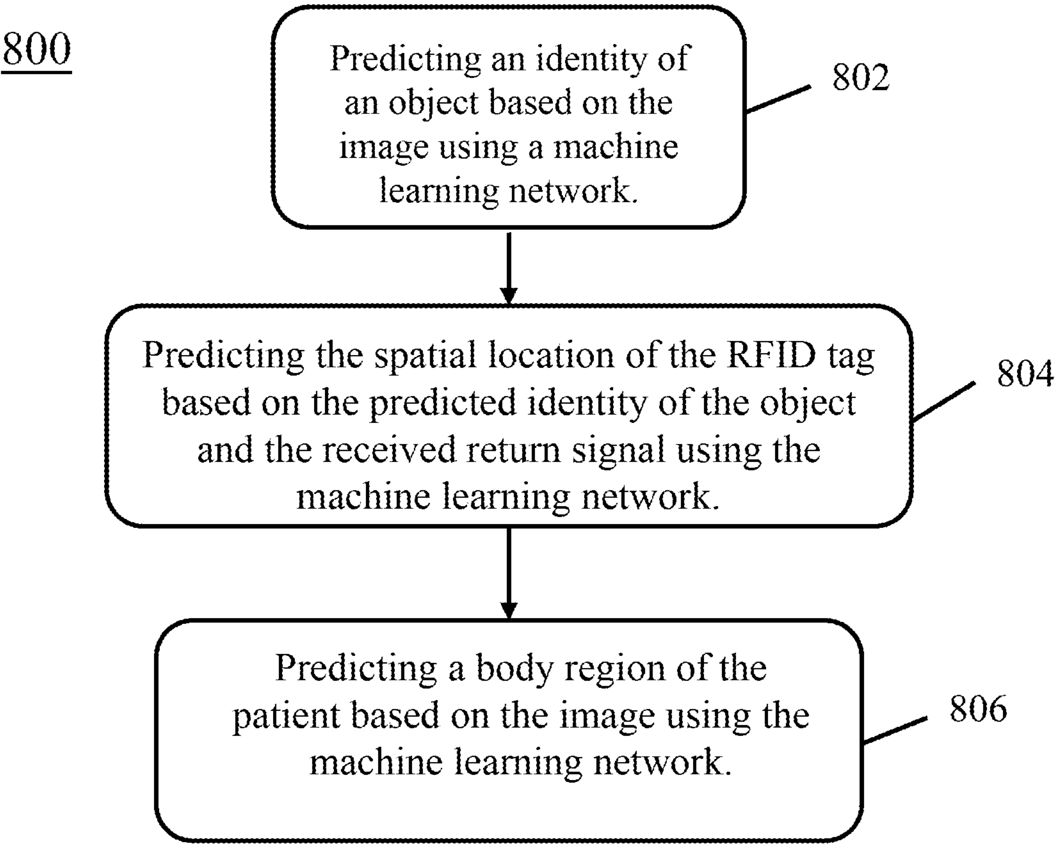
FIG. 7 is a flow chart of a computer-controlled method for determining a body region where the potentially retained surgical items is located using the system of FIG. 1.

The controller 200 may use machine learning (and/or other computer vision techniques) to analyze the images and classify what region of the patient's body 18 the antenna 110 is scanning based on the image (FIG. 5). In aspects, at operation 802 (FIG. 7) the controller 200 may predict an identity of an object 100*a* based on the image using a machine learning network 600 such as the machine learning network of FIG. 5. For example, based on a unique identifier (e.g., a serial number), the controller 200 may determine that the object 100*a* is a specific surgical sponge. In aspects, at operation 804 (FIG. 7) the controller 200 may predict the spatial location of the RFID tag 100 based on the predicted identity of the object 100*a* and the received signal using the machine learning network. At operation 806, (FIG. 7) the controller 200 may predict a body region of the patient 18 based on the image using the machine learning network.

It is contemplated that the inventory system 10 may be used to ensure proper scanning technique and ensure clinicians are scanning the correct body part for the correct surgery. The correct surgery and body part may be determined based on electronic medical record connectivity and on the determined body part.

In aspects, the controller 200 may display the determined spatial location of the RFID tag 100 on a display 140 (FIG. 1). For example, at operation 906 (FIG. 8) the image data may be combined with a presence or absence of RFID tag 100 detection in a region or the strength of an RFID tag 100 signal in the observed region. At operation 908 (FIG. 8) controller 200 may generate a list of regions with detections as a heat map of at least a portion of the body of the patient showing the regions scanned and the image of the area. The resultant data may be presented to the operator 12, for example, as the list of regions with detections, as a heat map of the patient's body 18 showing the regions scanned and presence, the absence, and/or the strength of detection for the region and/or the image(s) of the region(s) with the detection(s). In an aspect, the controller 200 may identify the type and number of unique detections for an observed region.

It is contemplated that the display 140 may be incorporated into the antenna 110, within a directly connected base station box, and/or may utilize a remotely connected display such as a remote screen or tablet.

It is contemplated that the processing of images may be conducted on the antenna handset 111, within a directly connected base station box or within a remote processing hub. In aspects, data transfer may be wired or wireless.

In aspects, at operation 904 of method 900 (FIG. 8), the controller 200 may enhance collected images for applications such as super resolution, deblurring, image correction, occlusion detection and removal, using the machine learning network 600 (FIG. 5).

With reference to FIG. 5, the controller 200 may include a machine-learning network 600 configured to make these evaluations. For example, the controller 200 may use machine learning to predict a body region of the patient 18 based on the image. For example, machine learning may include a convolutional neural network (CNN) and/or a state variant machine (SVM). The CNN may be trained on previous images of patients and RFID tags. In aspects, the machine-learning network 600 used would run through the scenario multiple times on its own, and the results may be gathered in addition to feedback and advice from potential experts in the field and then combined to determine which routes on a scenario would wield the greatest results. The machine learning network 600 may be trained using supervised training and/or unsupervised training. The machine-learning network may additionally predict 606 the spatial location of the RFID tag 100 based on the predicted identity of the object 100*a* and the received signal, and/or any other suitable parameter or metric.

Figure 6:
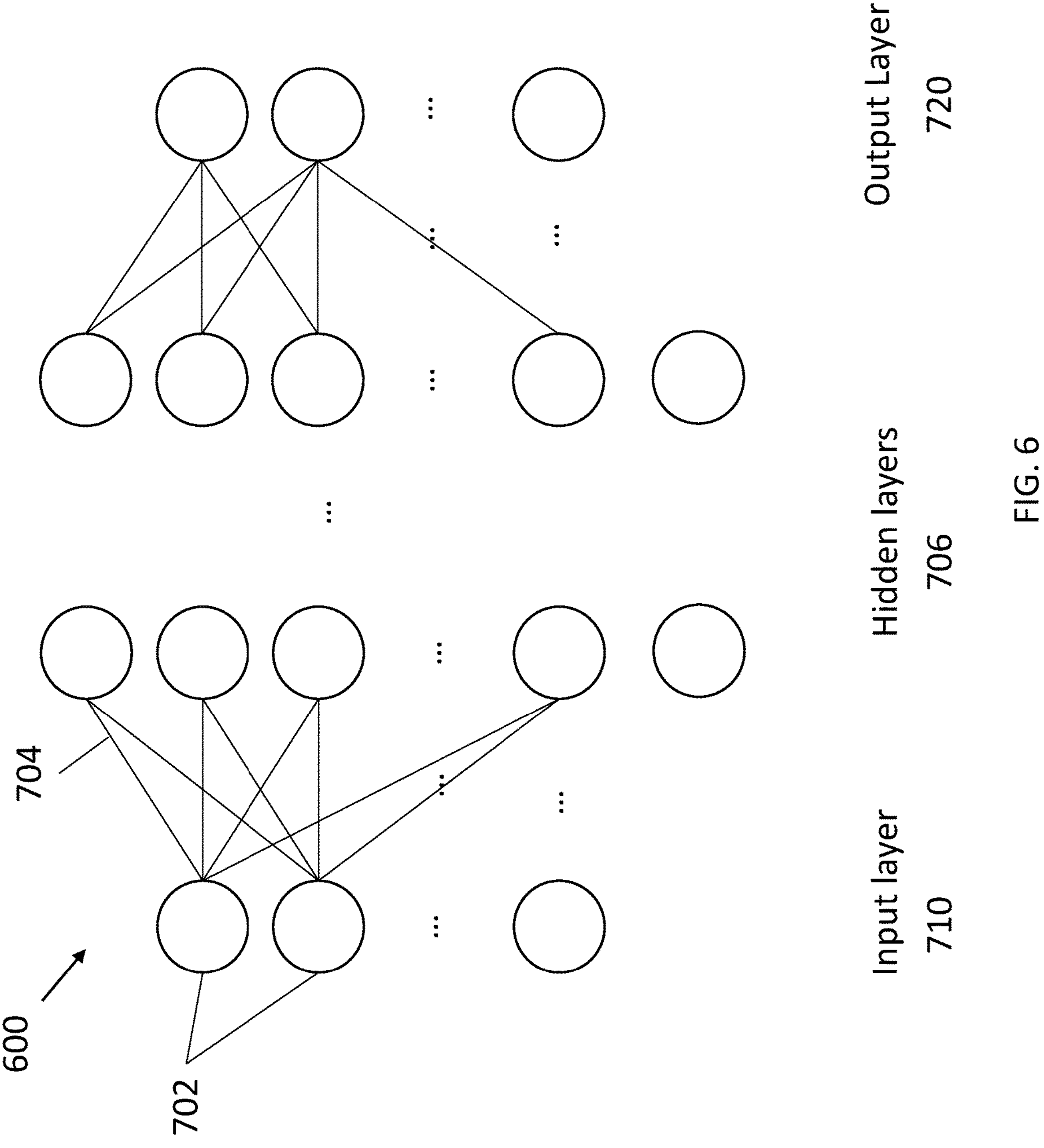
FIG. 6 is a diagram of layers of a neural network of FIG. 5 in accordance with aspects of the disclosure.

Referring to FIG. 6, generally, the machine-learning network 600 (e.g., a convolutional deep learning neural network) of FIG. 5 includes at least one input layer 710, a plurality of hidden layers 706, and at least one output layer 720. The input layer 710, the plurality of hidden layers 706, and the output layer 720 all include neurons 702 (e.g., nodes). The neurons 702 between the various layers are interconnected via weights 674. Each neuron 702 in the machine-learning network 600 computes an output value by applying a specific function to the input values coming from the previous layer. The function that is applied to the input values is determined by a vector of weights 704 and a bias. Learning, in the deep learning neural network, progresses by making iterative adjustments to these biases and weights. The vector of weights 704 and the bias are called filters (e.g., kernels) and represent particular features of the input (e.g., a particular shape). The machine-learning network 600 may output logits.

While several aspects of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting but merely as exemplifications of particular aspects. Those skilled in the art will envision other modifications within the scope of the claims appended hereto.

What is claimed is:

1. An inventory system configured for detecting and counting potentially retained surgical items, the inventory system comprising:

a Radio Frequency Identification (RFID) tag configured to transmit a return signal when energized;

a signal generator configured to generate an energizing signal for the RFID tag;

an antenna operably coupled to the signal generator, the antenna configured to receive at least one return signal transmitted by the RFID tag, the antenna includes an imaging device configured to capture an image of an area including at least a portion of a body of a patient, a location of the imaging device is on a loop of the antenna, a display is incorporated into the antenna, and the antenna includes a gyro and a global positioning system (GPS);

a processor; and a memory, including instructions stored thereon, which when executed by the processor cause the system to:

energize the RFID tag;

receive the return signal from the antenna;

capture the image of the area including at least the portion of the body of the patient from the imaging device;

enhance the captured image using a machine learning network configured for at least one of: deblurring, image correction, or occlusion detection and removal;

combine the image of the area with a presence of RFID tag detection in a region, an absence of RFID tag detection in the region, or a strength of an RFID tag signal in the region;

determine a spatial location of the RFID tag based on the image and the received signal; and display, on the display, a list of regions with detections as a heat map of at least a portion of the body of the patient showing the regions scanned and the image of the area, the strength of detection for the region, together with the detections.

2. The system of claim 1, wherein the instructions, when executed by the processor, further cause the system to display the determined spatial location of the RFID tag on the display.

3. The system of claim 1, wherein the RFID tag includes a unique identifier.

4. The system of claim 3, wherein the instructions, when executed by the processor, further cause the system to determine at least one characteristic of the RFID tag based on the unique identifier.

5. The system of claim 4, wherein the instructions, when executed by the processor, further cause the system to determine a quantity of unique RFID tags based on the unique identifier of each unique RFID tag of the quantity of RFID tags.

6. The system of claim 1, wherein the RFID tag includes a visual marker.

7. The system of claim 6, wherein the captured image includes the visual marker, and wherein the instructions, when executed by the processor, further cause the system to determine a unique characteristic of the RFID tag based on the visual marker.

8. The system of claim 1, wherein the instructions, when executed by the processor, further cause the system to predict an identity of an object based on the image using the machine learning network.

9. The system of claim 8, wherein when determining the spatial location of the RFID tag the instructions, when executed by the processor, further cause the system to predict the spatial location of the RFID tag based on the predicted identity of the object and the received signal using the machine learning network.

10. The system of claim 1, wherein the instructions, when executed by the processor, further cause the system to predict a body region of the patient based on the image using the machine learning network.

11. The system of claim 1, wherein the instructions, when executed by the processor, further cause the system to:

identify a type and number of unique detections for the region.

12. A computer-implemented method for detecting and counting potentially retained surgical items within a body of a patient, the method comprising:

energizing a Radio Frequency Identification (RFID) tag, the RFID tag configured to transmit a return signal when energized;

receiving the return signal using an antenna, the antenna operably coupled to a signal generator, the antenna includes an imaging device and a gyro and a global positioning system (GPS), a location of the imaging device is at least one of on a patient-facing side of a handset of the antenna or on a loop of the antenna, and a display is incorporated into the antenna;

capturing, using the imaging device, an image of an area including at least a portion of the body of the patient;

enhancing the captured image using a machine learning network configured for at least one of: deblurring, image correction, or occlusion detection and removal; and determining a spatial location of the RFID tag based on the image and the received return signal by:

predicting an identity of an object based on the image using the machine learning network;

predicting the spatial location of the RFID tag based on the predicted identity of the object and the received return signal using the machine learning network; and displaying, on the display, a list of regions with detections as a heat map of at least a portion of the body of the patient showing the regions scanned and the image of the area, the strength of detection for the region, together with the detections.

13. The computer-implemented method of claim 12, further comprising:

displaying the determined spatial location of the RFID tag on the display.

14. The computer-implemented method of claim 12, wherein the RFID tag includes a unique identifier.

15. The computer-implemented method of claim 14, further comprising:

determining at least one characteristic of the RFID tag based on the unique identifier.

16. The computer-implemented method of claim 15, further comprising:

determining a quantity of unique RFID tags based on the unique identifier of each unique RFID tag of the quantity of RFID tags.

17. The computer-implemented method of claim 12, wherein the RFID tag includes a visual marker, wherein the captured image includes the visual marker, and wherein the method further includes determining a unique characteristic of the RFID tag based on the visual marker.

18. The method of claim 12, further comprising:

combine the image of the area with a presence of RFID tag detection in a region, an absence of RFID tag detection in the region, and a strength of an RFID tag signal in the region.

19. A non-transitory computer-readable medium storing instructions which, when executed by a processor, cause the processor to perform a method for detecting and counting potentially retained surgical items within a body of a patient, comprising:

energizing an RFID tag, the RFID tag configured to transmit a return signal when energized;

receiving the return signal using an antenna, the antenna operably coupled to a signal generator, the antenna includes an imaging device and at a gyro and a global positioning system (GPS), a location of the imaging device is at least one of on a patient-facing side of a handset of the antenna or on a loop of the antenna, and a display is incorporated into the antenna;

capturing, using the imaging device, an image of an area including at least a portion of the body of the patient;

enhancing the captured image using a machine learning network configured for at least one of: deblurring, image correction, or occlusion detection and removal; and determining a spatial location of the RFID tag based on the image and the received return signal by:

predicting an identity of an object based on the image using the machine learning network;

predicting the spatial location of the RFID tag based on the predicted identity of the object and the received return signal using the machine learning network; and displaying, on the display, a list of regions with detections as a heat map of at least a portion of the body of the patient showing the regions scanned and the image of the area, the strength of detection for the region, together with the detections.

* * * * *